United States Patent
Tayama

(10) Patent No.: US 10,384,647 B2
(45) Date of Patent: Aug. 20, 2019

(54) ELECTRONIC KEY SYSTEM

(71) Applicants: Shuichi Tayama, Tokyo (JP); IMAGE CO., LTD., Tokyo (JP)

(72) Inventor: Shuichi Tayama, Tokyo (JP)

(73) Assignees: Shuichi Tayama, Tokyo (JP); IMAGE CO., LTD., Tokyo (JP)

(*) Notice: Subject to any disclaimer, the term of this patent is extended or adjusted under 35 U.S.C. 154(b) by 0 days.

(21) Appl. No.: 15/755,369

(22) PCT Filed: Aug. 18, 2016

(86) PCT No.: PCT/JP2016/074125
§ 371 (c)(1),
(2) Date: Feb. 26, 2018

(87) PCT Pub. No.: WO2017/038485
PCT Pub. Date: Mar. 9, 2017

(65) Prior Publication Data
US 2018/0272991 A1 Sep. 27, 2018

(30) Foreign Application Priority Data
Aug. 28, 2015 (JP) .................................. 2015-168531

(51) Int. Cl.
*G05B 19/00* (2006.01)
*B60R 25/25* (2013.01)
(Continued)

(52) U.S. Cl.
CPC .......... *B60R 25/252* (2013.01); *A61B 5/1172* (2013.01); *B60R 25/24* (2013.01);
(Continued)

(58) Field of Classification Search
USPC ....................................................... 340/5.53
See application file for complete search history.

(56) References Cited

U.S. PATENT DOCUMENTS

2004/0113771 A1* 6/2004 Ozaki ................. A61B 5/0002
340/539.12
2005/0162254 A1 7/2005 Michishige et al.
(Continued)

FOREIGN PATENT DOCUMENTS

JP 2005-139700 A 6/2005
JP 2008-009585 A 1/2008
(Continued)

OTHER PUBLICATIONS

PCT/ISA/210, "International Search Report for International Application No. PCT/JP2016/074125" dated Oct. 4, 2016.

*Primary Examiner* — Kerri L McNally
*Assistant Examiner* — Thang D Tran
(74) *Attorney, Agent, or Firm* — Manabu Kanesaka

(57) ABSTRACT

Provided is an electronic key system capable of providing an instruction to an automobile through a portable device having biometric authentication of a user. When biometric information of a wearer is detected by a biometric recognition sensor, a portable device worn on a user determines with a biometric authentication unit whether or not the detected biometric information is matched with biometric information of a previously-registered user. When the biometric authentication unit authorizes that the wearer is a registered user, the portable device enables, through a communication control unit, near-distance wireless communication with a control unit mounted on an automobile through a wireless communication device. Thus, the portable device can provide an operational instruction to the automobile through wireless communication with the control unit.

14 Claims, 12 Drawing Sheets

(51) Int. Cl.
   *A61B 5/1172*   (2016.01)
   *E05B 49/00*    (2006.01)
   *B60R 25/24*    (2013.01)
   *G06F 21/32*    (2013.01)

(52) U.S. Cl.
   CPC .............. *B60R 25/25* (2013.01); *E05B 49/00*
                     (2013.01); *G06F 21/32* (2013.01)

(56) References Cited

U.S. PATENT DOCUMENTS

| | | | | |
|---|---|---|---|---|
| 2006/0104504 A1* | 5/2006 | Sung | ................ | G06K 9/00281 |
| | | | | 382/159 |
| 2010/0039224 A1* | 2/2010 | Okude | ................ | B60R 25/25 |
| | | | | 340/5.83 |
| 2010/0148923 A1* | 6/2010 | Takizawa | ............ | B60R 25/2018 |
| | | | | 340/5.82 |
| 2011/0215900 A1* | 9/2011 | Corradino | ................ | 340/5.53 |
| 2012/0164989 A1* | 6/2012 | Xiao | ................ | G07C 5/008 |
| | | | | 455/414.1 |
| 2013/0098995 A1* | 4/2013 | Jurek | ................ | G06Q 20/3223 |
| | | | | 235/380 |
| 2013/0200995 A1* | 8/2013 | Muramatsu | ............. | B60R 25/24 |
| | | | | 340/5.51 |
| 2014/0070943 A1* | 3/2014 | Breed | ................ | E05F 15/43 |
| | | | | 340/539.11 |
| 2014/0266153 A1* | 9/2014 | Fujiwara | ................ | G01R 21/00 |
| | | | | 324/103 R |
| 2014/0313011 A1* | 10/2014 | Mimura | ............. | G07C 9/00309 |
| | | | | 340/5.64 |
| 2014/0342667 A1* | 11/2014 | Aarnio | ................ | H04W 12/06 |
| | | | | 455/41.2 |
| 2014/0359499 A1* | 12/2014 | Cho | ................ | G06F 8/38 |
| | | | | 715/765 |
| 2014/0368336 A1* | 12/2014 | Felix | ................ | H04W 4/90 |
| | | | | 340/539.13 |
| 2015/0025917 A1* | 1/2015 | Stempora | ............... | G06Q 40/08 |
| | | | | 705/4 |
| 2015/0055822 A1* | 2/2015 | Zhou | ................ | G06F 3/017 |
| | | | | 382/103 |
| 2015/0120151 A1* | 4/2015 | Akay | ................ | B60R 25/24 |
| | | | | 701/49 |
| 2015/0135310 A1* | 5/2015 | Lee | ................ | A61B 5/681 |
| | | | | 726/20 |
| 2015/0149018 A1* | 5/2015 | Attard | ................ | G05D 1/0061 |
| | | | | 701/23 |
| 2015/0288687 A1* | 10/2015 | Heshmati | ............ | H04L 63/0861 |
| | | | | 726/7 |
| 2015/0304322 A1* | 10/2015 | Zaidi | ................ | G06K 9/00892 |
| | | | | 382/115 |
| 2015/0347734 A1* | 12/2015 | Beigi | ................ | G06F 21/32 |
| | | | | 713/155 |
| 2015/0350207 A1* | 12/2015 | Kim | ................ | H04L 63/105 |
| | | | | 713/170 |
| 2015/0362997 A1* | 12/2015 | Hatton | ................ | G06F 3/017 |
| | | | | 701/2 |
| 2015/0363986 A1* | 12/2015 | Hoyos | ................ | G07C 9/00563 |
| | | | | 340/5.61 |
| 2015/0379793 A1* | 12/2015 | Murakami | ............ | B60R 25/24 |
| | | | | 340/5.61 |
| 2016/0127900 A1* | 5/2016 | John Archibald | .... | H04W 12/06 |
| | | | | 726/7 |
| 2016/0371907 A1* | 12/2016 | Ma | ................ | E05B 81/82 |

FOREIGN PATENT DOCUMENTS

| | | |
|---|---|---|
| JP | 2008-189261 A | 8/2008 |
| JP | 2014-148842 A | 8/2014 |
| JP | 2015-074311 A | 4/2015 |

* cited by examiner

FIG. 3
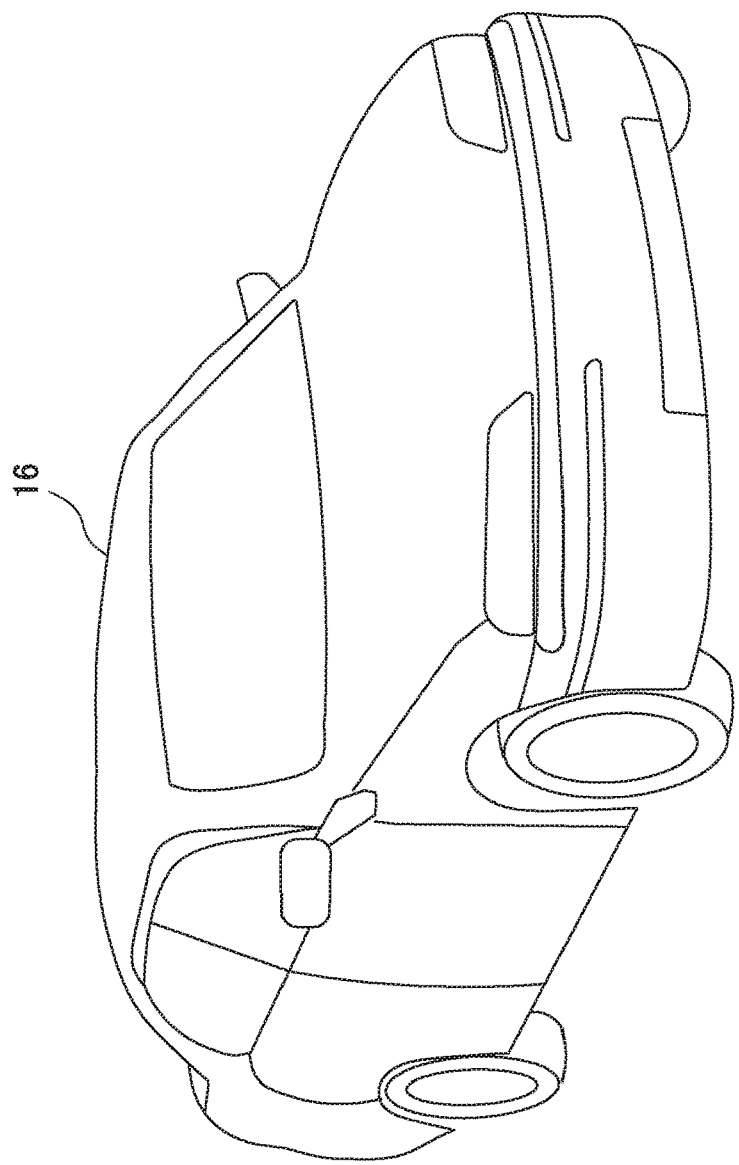
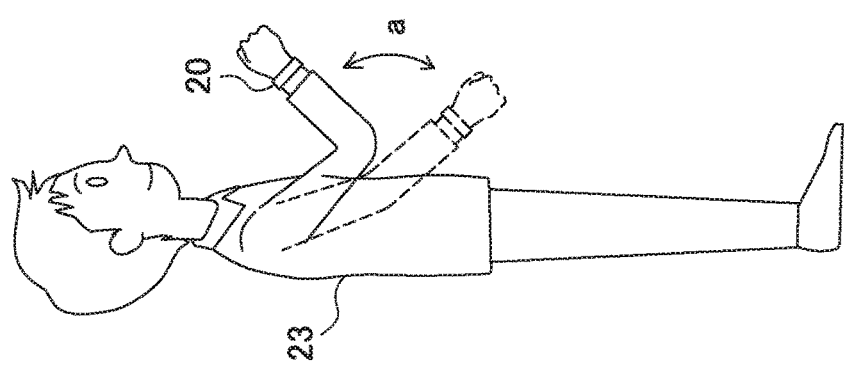

FIG. 4

| Action type | Operational instruction |
|---|---|
| Vertical reciprocating swing action | Door lock releasing |
| Horizontal reciprocating swing action | Door locking |
| Vertical reciprocating linear action | Engine starting |
| Horizontal reciprocating linear action | Engine stopping |

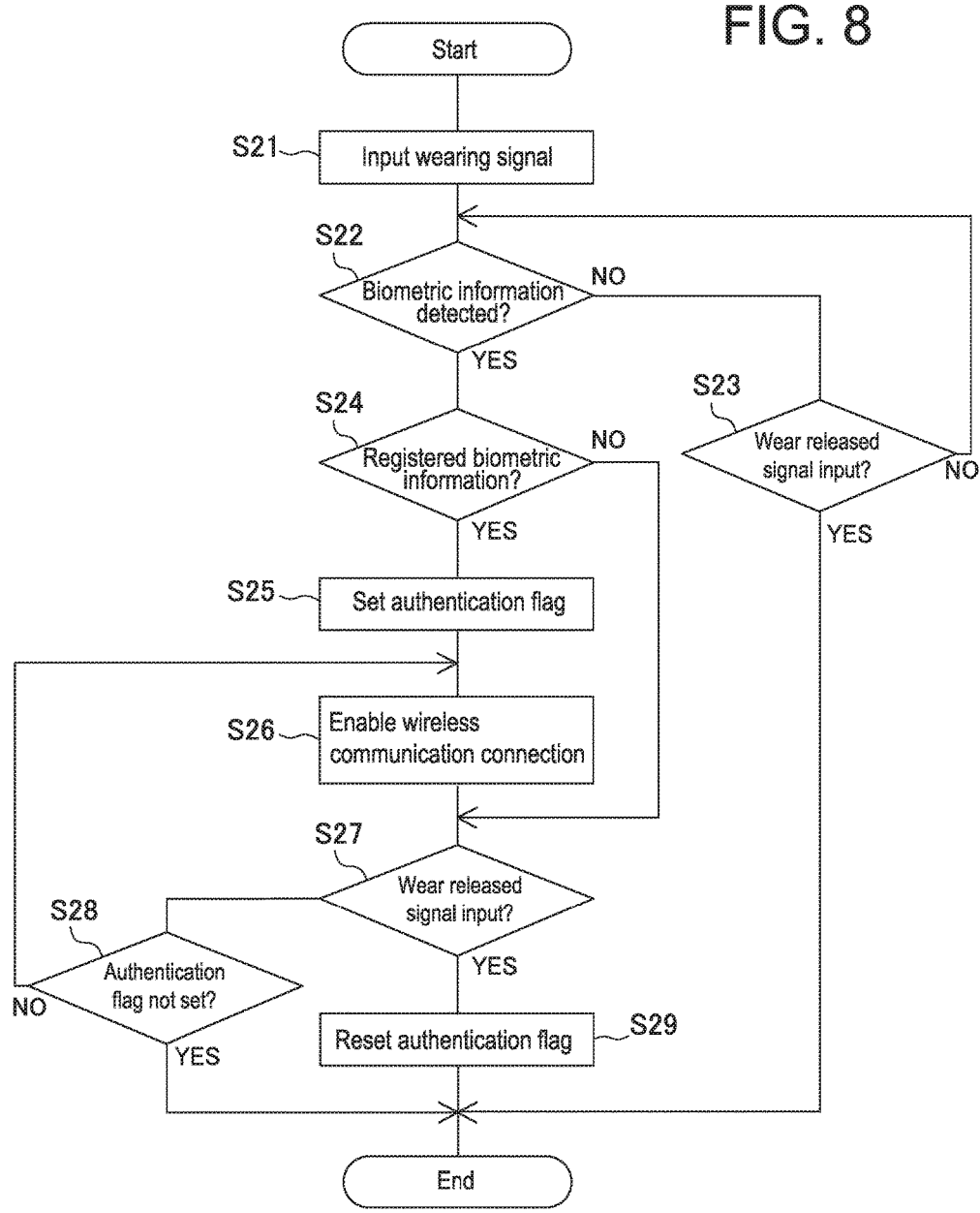

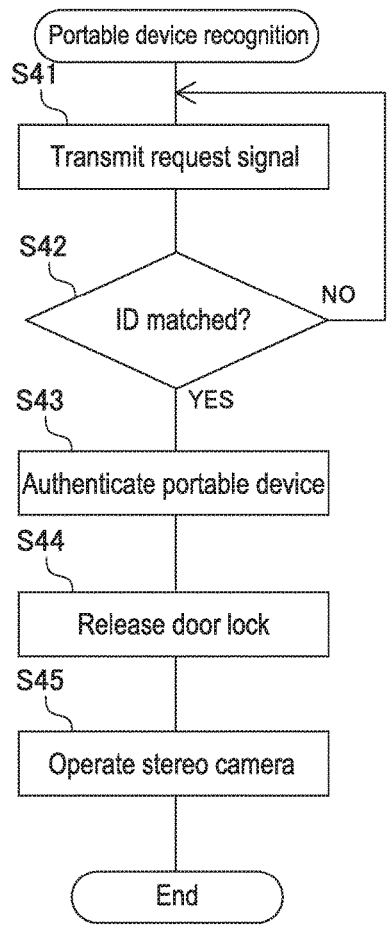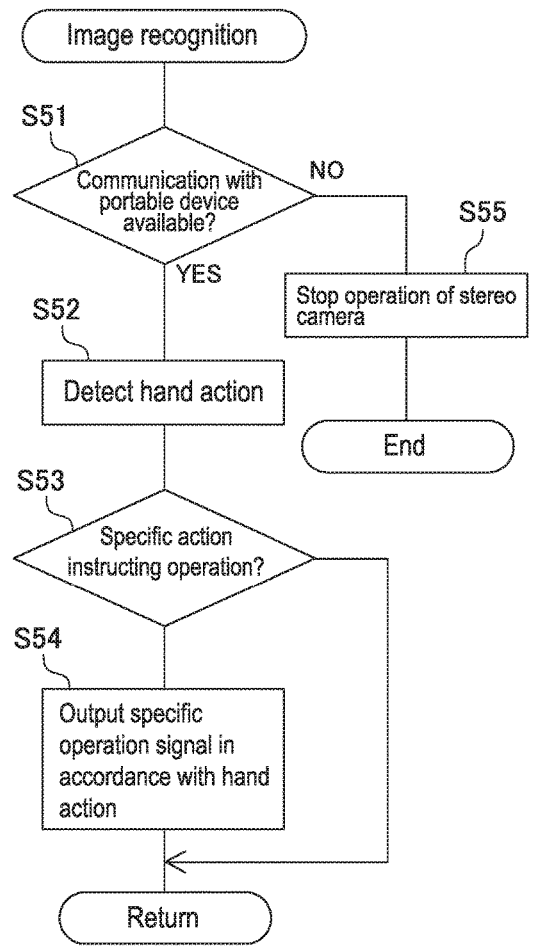
FIG. 9A
FIG. 9B

ELECTRONIC KEY SYSTEM

RELATED APPLICATIONS

The present application is National Phase of International Application No. PCT/JP2016/074125 filed Aug. 18, 2016, and claims priority from Japanese Application No. 2015-168531, filed Aug. 28, 2015, the disclosure of which is hereby incorporated by reference herein in its entirety.

TECHNICAL FIELD

The present invention relates to an electronic key system, and in particular, relates to an electronic key system that enables an authorized user to provide operational instructions to an automobile.

BACKGROUND ART

Recently, there has been developed an electronic key system that enables, without being inserted, to lock/unlock a door of an automobile, to start/stop an engine, and the like.

As such an electronic key system, there has been disclosed a biometric authentication key system, for ensuring security, with which a removable data storage device to store biometric information of a registrant as registration information is set in an automobile body and locking/unlocking of a door and driving of the automobile can be performed when biometric information obtained from an occupant for the automobile matches the registration data (e.g., see Patent Literature 1).

CITED LITERATURE

Patent Literature

Patent Literature 1: Japanese Patent Application Laid-Open No. 2008-9585

SUMMARY OF THE INVENTION

In Patent Literature 1 of the related art, door lock is released in the case that biometric information obtained from a first biometric sensor arranged at an outer handle of the door when a user grasps the outer handle matches registration information, and then, driving of the automobile can be performed in the case that biometric information obtained from a second biometric sensor arranged at an instrument panel is matched with registered information. Here, since biometric sensors are required to be arranged in accordance with instructions to the automobile, there has been a problem of cost increasing.

In view of the above, the present invention provides an electronic key system that enables to provide instructions to an automobile through a portable device having biometric authentication of a user.

The present invention provides an electronic key system configured to provide an operational instruction to a control unit mounted on an automobile with a portable device worn on and carried by a region of a user. The electronic key system includes a registered biometric information storage unit configured to store biometric information of a previously-registered user, and a biometric authentication unit configured to determine whether or not biometric information of the user is matched with the previously-registered biometric information of the user. Here, the portable device includes at least a biometric recognition sensor configured to detect biometric information of the user, and authentication between the portable device and the control unit is established when the user is authorizes as the registered user by the biometric authentication unit.

Further, the portable device includes a wear detection unit. Then, the biometric authentication unit performs determination of matching with the biometric information when the wear detection unit detects wearing onto the user and establishes authentication between the portable device and the control unit when the biometric information is matched. Here, it is preferable that the biometric authentication unit releases the authentication when the wear detection unit detects that the user has removed the portable device after establishment of the authentication. According to the above, only a person who wears the portable device can provide an instruction to the automobile.

Further, it is preferable that the portable device includes an action detection unit configured to detect an action of a region of the user with the portable device worn, and an operation instruction unit configured to perform controlling to generate an operation code to the automobile in accordance with a specific action of the region detected by the action detection unit and to transmit the operation code from the wireless communication device. According to the above, the user can provide an instruction with an action of a body region on which the portable device is worn.

Further, the control unit may include a portable device recognition unit configured to recognize the portable device with which the user is authorized as the registered user by the biometric authentication unit, an imaging device configured to image an action of the user, an image recognition unit configured to detect a specific action of the user based on the image information from the imaging device, and an operation control unit configured to control an operation of the automobile in accordance with the detected specific action. In this case, an instruction can be provided to the automobile by performing an image recognition process on an action of the authorized registered user.

Further, the biometric information storage unit and the biometric authentication unit may be arranged at a cloud server. In this case, owing to that the control unit transmits the biometric information transmitted from the portable device to the cloud server, it is possible to establish authentication with the portable device based on a determination result of the biometric authentication unit.

On the other hand, it is also possible that the portable device transmits the biometric information to the cloud server and establishes authentication with the control unit based on a determination result of the biometric authentication unit. By utilizing such a cloud server, it is possible to establish authentication between a single portable device and a plurality of control units of automobiles.

Further, owing to that the biometric information storage unit further stores preference information regarding automobile driving of the user corresponding to the stored biometric information, the control unit can download the preference information when authentication with the portable device is established. According to the above, the control unit can control operations of the automobile in accordance with preference of the user.

According to the electronic key system of the present invention, biometric information of a user is obtained on the side of the portable device. Accordingly, it is possible to provide an electronic key system with simplified biometric authentication that does not require a plurality of biometric recognition sensors to be arranged in an automobile in accordance with operational instructions

BRIEF DESCRIPTION OF THE DRAWINGS

FIG. 3 is a schematic view illustrating a state to provide an instruction to an automobile by an action of an arm wearing the portable device.

FIG. 4 is an operational instruction table indicating correspondence between types of arm actions and operational instructions to the automobile indicated by the actions.

FIG. 8 is a flowchart of operations of a portable device of the electronic key system in FIG. 6.

FIGS. 9A and 9B are flowcharts of operations of a control unit of the automobile in the electronic key system in FIG. 6.

EMBODIMENTS OF THE INVENTION

In the following, embodiments of an electronic key system according to the present invention will be described with reference to the drawings.

Figure 1:
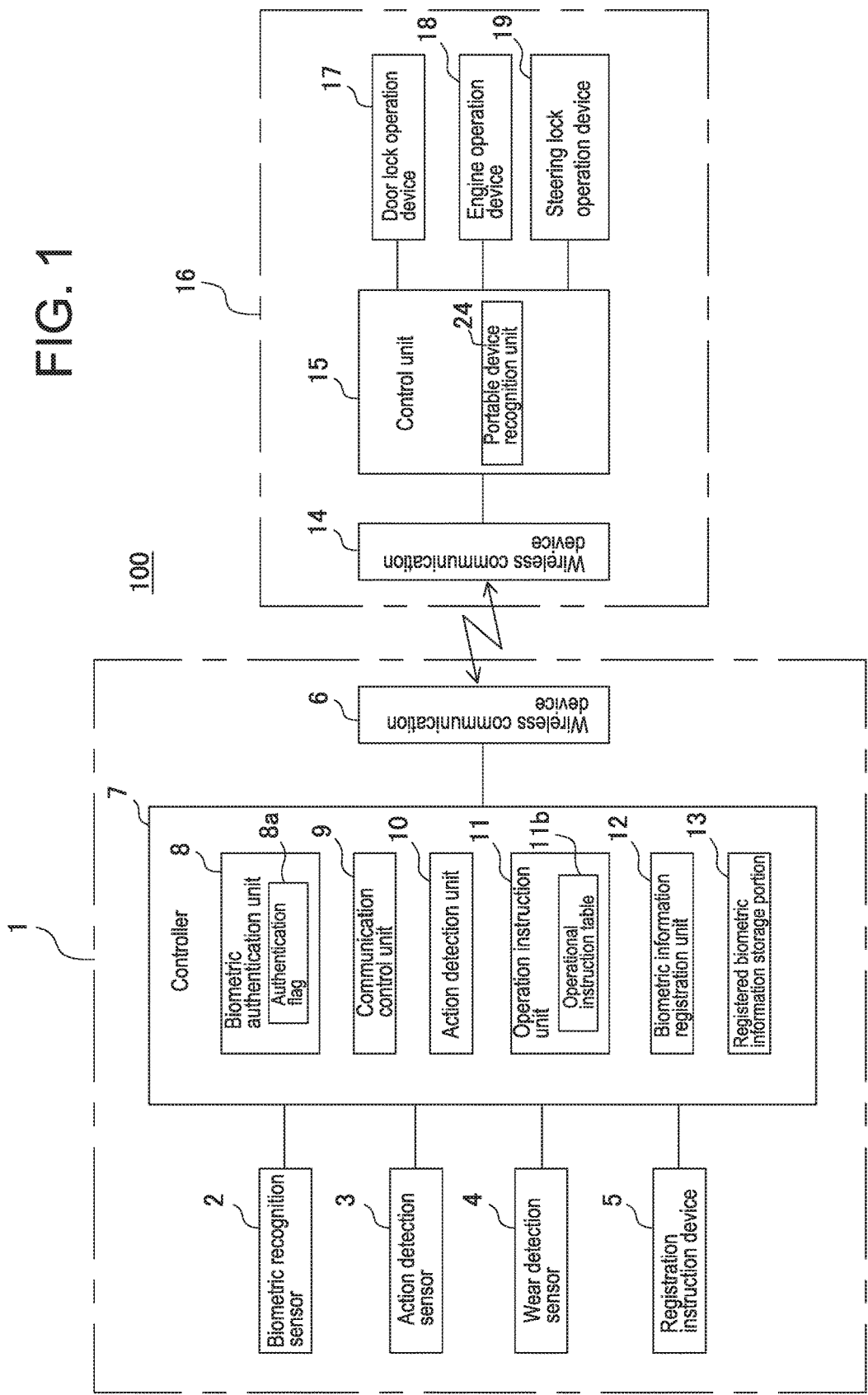
FIG. 1 is a block diagram illustrating an entire configuration of an electronic key system of a first embodiment of the present invention.

FIG. 1 is a block diagram schematically illustrating an entire configuration of an electronic key system 100. The electronic key system 100 wirelessly provides operational instructions to an automobile 16. The electronic key system 100 includes a portable device 1 to be carried by a user and a control unit 15 mounted on the automobile 16.

Figure 2:
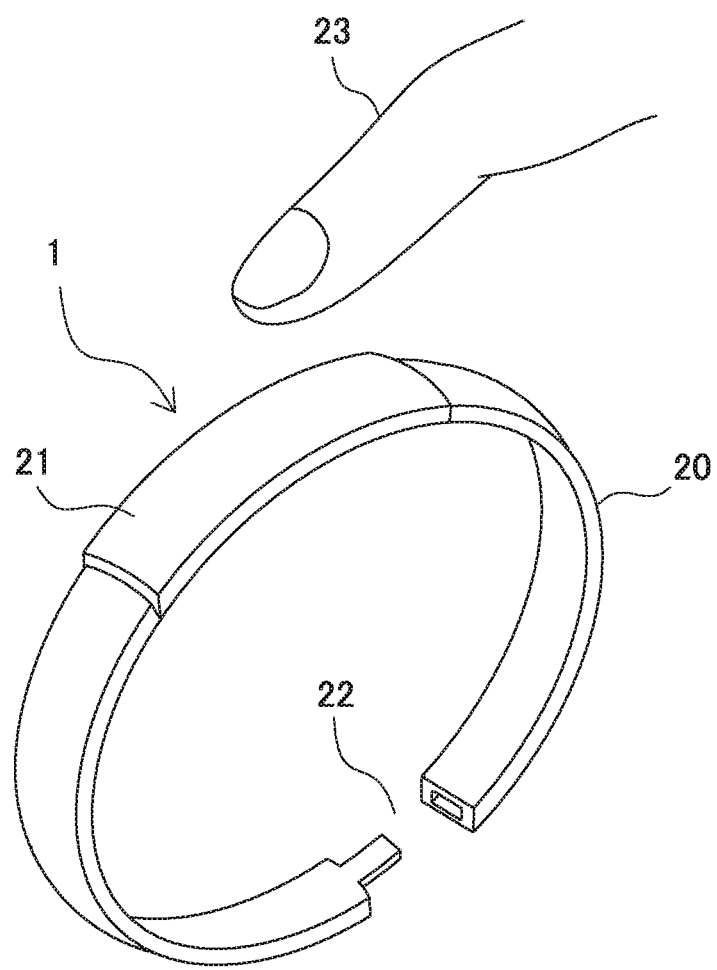
FIG. 2 is an external view of a structural example of a bracelet-type portable device.

As illustrated in FIGS. 2 and 3, the portable device 1 is mounted on a bracelet 20 to be wearable on an arm of a user. The portable device 1 includes a biometric recognition sensor 2, an action detection sensor 3, a wear detection sensor 4 that detects wearing of the bracelet 20 on the user, a registration instruction device 5, a wireless communication device 6, and a controller 7.

The biometric recognition sensor 2 detects biometric information such as a fingerprint, a finger vein pattern, and heart beating. The biometric sensor 2 of the present example is a fingerprint sensor. The biometric sensor 2 detects a fingerprint as biometric information when a fingerprint part of a finger 23 of a person is pressed to a surface 21 of the portable device 1.

The action detection sensor 3 detects a movement amount and a movement angle of the portable device 1 caused by an arm action of a user who is wearing the portable device 1. Such an action detection sensor 3 adopts either or both of an acceleration sensor and an angular velocity sensor. In the present example, both the acceleration sensor and the angular velocity sensor are used to detect a movement amount and angular velocity in three axes.

The wear detection sensor 4 outputs a wearing signal when the bracelet 20 is worn on a user's arm and both ends thereof are connected with a buckle 22 and outputs a wear released signal when the connection is released.

The wireless communication device 6 performs wireless communication in near field with the control unit 15 of the automobile 16 in radio frequency range. In this case, wireless communication becomes available when the control unit 15 determines that the portable device 1 existing in the wireless communication field has been registered in advance.

The controller 7 is structured with a computer including a CPU, a ROM, and a RAM. A biometric authentication unit 8, a communication control unit 9, an action detection unit 10, an operation instruction unit 11, and a biometric information registration unit 12 are actualized respectively by the CPU executing control programs stored in the ROM. Further, the controller 7 includes a registered biometric information storage portion 13 configured of a flash memory that stores the registered biometric information.

The biometric information registration unit 12 stores biometric information (fingerprint information in the present example) detected by the biometric recognition sensor 2 in the registered biometric information storage portion 13 configured of the flash memory in accordance with a registration instruction signal from the registration instruction device 5. In this case, plural pieces of biometric information can be registered in the registered biometric information storage portion 13. The registration instruction device 5 is configured of a switch device that outputs a registration instruction signal with a predetermined operation by a registrant. Here, in view of security, it is preferable that the registration instruction device 5 is arranged separately from the portable device 1 normally, and is used as being connected to the portable device 1 at the time of registration setting.

When the bracelet 20 is worn on a user's arm and the biometric recognition sensor 2 detects biometric information, the biometric authentication unit 8 compares the detected biometric information and the registered biometric information stored in the registered biometric information storage portion 13 and determines whether or not both thereof are matched with each other. When both thereof are matched with each other, an authentication flag 8a is set in the RAM.

The communication control unit 9 performs transmitting and receiving of signals for authentication between the portable device 1 and the control unit 15 of the automobile 16.

When the action detection sensor 3 detects a movement amount and a movement angle of the portable device 1 caused by an action of a user's arm, the action detection unit 10 calculates a moved position of the portable device 1 from the detection information. Subsequently, when the action detection sensor 3 detects a movement amount and a movement angle of the portable device 1 caused again by an action of the user's arm immediately after the above and a moved position calculated from the detection information is the original position, the action detection unit 10 determines that the user has moved the arm in a reciprocating manner. FIG. 3 schematically illustrates a state in which a wearer 23 has swung the arm upward and downward in a direction of arrow a with the elbow being as a fulcrum.

The operation instruction unit 11 determines a previously-set operational instruction to be provided to the automobile 16 in accordance with the reciprocating action detected by the action detection unit 10, generates an operation code indicating the instruction, and transmits the operation code to the control unit 15 of the automobile 16 through the wireless communication device 6. An operational instruction table 11b indicating correspondence between types of reciprocating actions to be detected by the action detection unit 10 and operational instructions to the automobile 16 indicated by the reciprocating actions is set in the ROM. For example, as illustrated in FIG. 4, the operational instruction table 11b includes operational instructions to be provided to the automobile 16 respectively by reciprocating swing actions in vertical and horizontal directions and reciprocating linear actions in vertical and horizontal directions of the portable device 1.

Accordingly, when the wearer 23 performs a vertical reciprocating swing action of the portable device 1 with the elbow being as a fulcrum as illustrated in FIG. 3, the operation instruction unit 11 reads out from the operational instruction table 11b that the action means an operational instruction to the automobile 16 to release door lock and transmits an operation code instructing the operation to the control unit 15.

The control unit 15 is a main controller of the automobile 16 being configured of a CPU. The control unit 15 performs control processes of electronic devices mounted on the automobile 16 based on execution of previously-set software. FIG. 1 illustrates only a portable device recognition unit 24 that directly relates to operations of the electronic key system 100 of the present invention. This function is actualized by executing the software.

The portable device recognition unit 24 intermittently transmits a request signal requesting the portable device 1 to transmit an ID through a wireless communication device 14. When the portable device 1 entering a transmittal range of the request signal receives the request signal through the wireless communication device 6 and transmits the ID in correspondence thereto, the portable device recognition unit 24 compares the ID with a previously-set ID. When those are matched, the portable device recognition unit 24 recognizes existence of the portable device 1.

When an operation code is input from the portable device 1 whose existence is recognized through the wireless communication device 14, the control unit 15 drives, in accordance with the operation code, a door lock operation device 17, an engine operation device 18, a steering lock operation device 19, and the like mounted on the automobile 16.

Figure 5:
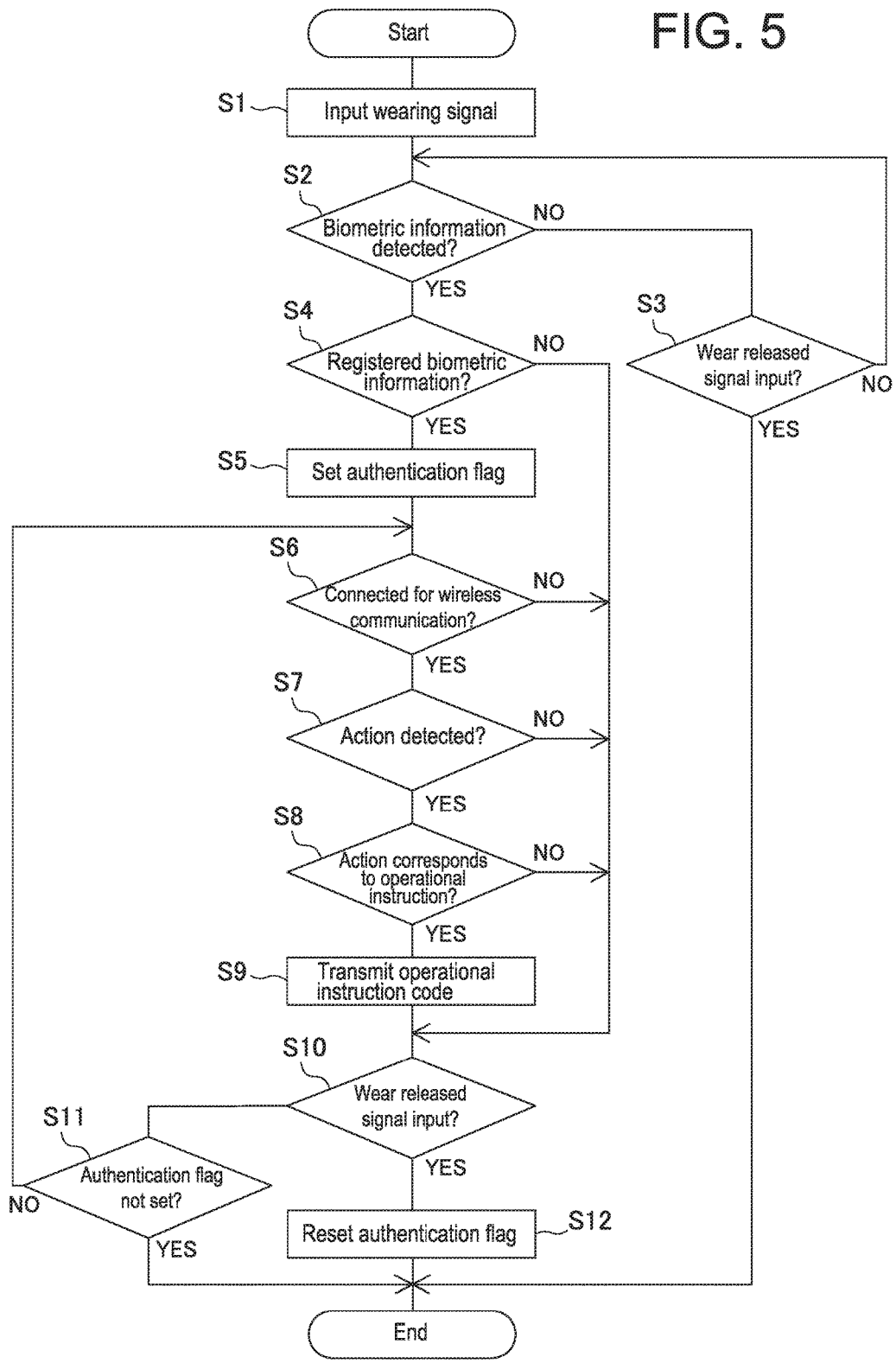
FIG. 5 is a flowchart of operations of the portable device in the electronic key system in FIG. 1.

Operations of the electronic key system 100 having the abovementioned configuration will be described with reference to a flowchart of FIG. 5.

When the bracelet 20 is wound to and worn on an arm of a user and the buckle 22 is engaged, a wearing signal is input to the controller 7 from the wear detection sensor 4 (step S1) and the portable device 1 starts to operate.

Then, the controller 7 determines with the biometric authentication unit 8 whether biometric information is detected by the biometric recognition sensor 2 (step S2). After the portable device 1 is worn, when the wearer 23 puts a finger on a package surface of the portable device 1, the biometric recognition sensor 2 outputs biometric information of a fingerprint. However, when a wear released signal is input from the wear detection sensor 4 before the biometric recognition sensor 2 outputs the biometric information ("YES" in step S3), the controller 7 ends the operation. This operation corresponds to a case that the portable device 1 is removed from the arm without placing a finger on the package surface of the portable device 1 after the portable device 1 is worn on the user.

When the wearer 23 places a finger on the package surface, the biometric authentication unit 8 compares the biometric information detected by the biometric recognition sensor 2 with registered biometric information stored in the registered biometric information storage portion 13 and determines whether or not the wearer 23 is a previously-registered user (step S4). In the case of "NO" that the wearer 23 is not a registered user with an unmatched comparison result, a process of step S10 described later is performed.

When the wearer 23 is authenticated as being a registered user with biometric information matching ("YES" in step S4), the biometric authentication unit 8 sets an authentication flag 8a indicating that the wearer 23 is the registered user (step S5).

Then, the controller 7 determines whether the communication control unit 9 is connected for wireless communication with the control unit 15 of the automobile 16 existing therearound (step S6). Here, when the wearer 23 approaches to the automobile 16, the communication control unit 9 receives a request signal transmitted by the control unit 15 with the portable device recognition unit 24. Then, the communication control unit 9 receives the request signal and transmits an ID in response thereto, so that wireless communication connection is established by the portable device recognition unit 24. Thus, authentication between the controller 7 and the control unit 15 is established.

If the wireless communication connection has been established by the portable device recognition unit 24 ("YES" in step S6), the controller 7 determines with the action detection unit 10 whether or not the portable device 1 has performed a reciprocating action (step S7). In the case that a moved position of the portable device 1 is calculated from a movement amount and a movement angle thereof output by the action detection sensor 3 and a moved position calculated from a movement amount and a movement angle subsequently output by the action detection sensor 3 is the original position before the movement, the action detection unit 10 determines that reciprocating motion has been performed. Here, the action detection unit 10 determines a type of the reciprocating action based on the movement amount and the movement angle detected by the action detection unit 10. It is determined to be a swing action if the movement angle varies and a linear action if the movement angle does not vary.

When the portable device 1 has performed a reciprocating action, the controller 7 refers, with the operation instruction unit 11, to the operational instruction table 11b based on the type of the reciprocating action determined by the action detection unit 10 and determines whether or not the reciprocating action is an action that corresponds to an operational instruction to the automobile 16 (step S8). When it is determined that the reciprocating action is an action that corresponds to an operational instruction, the operation instruction unit 11 outputs an operation code indicating the instruction to the control unit 15 of the automobile 16 (step S9).

In the example of FIG. 3, the wearer 23 performs an action to swing upward the arm on which the portable device 1 is worn as indicated by arrow a with the elbow being as a fulcrum. The operation instruction unit 11 determines that the action corresponds to an instruction to release door lock of the automobile 16 and transmits an operation code of door lock releasing to the control unit 15. The control unit 15 that has received the operation code outputs a drive signal to the door lock operation device 17, so that door lock is released.

In contrast, when the wearer 23 performs an action to swing downward the portable device 1, the operation instruction unit 11 determines that the action corresponds to an instruction to perform door locking of the automobile 16 and transmits an operation code of door locking to the control unit 15. According to the operational instruction table 11b of the present example, when a user linearly lifts the arm on which the portable device 1 is worn, the action corresponds to engine starting. The operation instruction unit 11 generates an operation code of engine starting and outputs the operation code to the control unit 15 of the automobile 16.

After the operation code is transmitted by the operation instruction unit 11, the controller 7 determines whether or not a wear released signal is input from the wear detection sensor 4 (step S10). When a wear released signal is not input ("NO" in step S10) and the authentication flag 8a is set ("NO" in step S11), processes from step S6 to step S11 are to be repeated. During the above, in a state that wireless communication connection is available ("YES" in step S6), when an action of the wearer 23 indicating an operational instruction is detected, an operation code corresponding thereto is transmitted to the control unit 15.

Similar to the above, when it is determined as "NO" in each determination process in steps S6, S7, S8, the processes from step S6 to step S11 are to be repeated as long as the portable device 1 remains worn on the arm of the wearer 23 and the authentication flag 8a is set.

Here, when the portable device 1 is removed from the arm of the wearer 23 and a wear released signal is input from the wear detection sensor 4 ("YES" in step S10), the controller 7 ends the operation after resetting the authentication flag 8a (step S12). Thus, authentication between the portable device 1 and the control unit 15 is released.

In contrast, entering step S11 without a wear released signal being input after entering step S10 as being determined as "NO" in step S4, the controller 7 ends the operation since the authentication flag 8b is not set in this case. That is, since the wearer 23 is not a registered user, operations are not performed even when the portable device 1 is worn.

In the above embodiment, the portable device 1 detects a specific action of a user and outputs, to the automobile 16, an operational code corresponding thereto. However, it is also possible to detect such a specific action of a user by the automobile 16.

Figure 6:
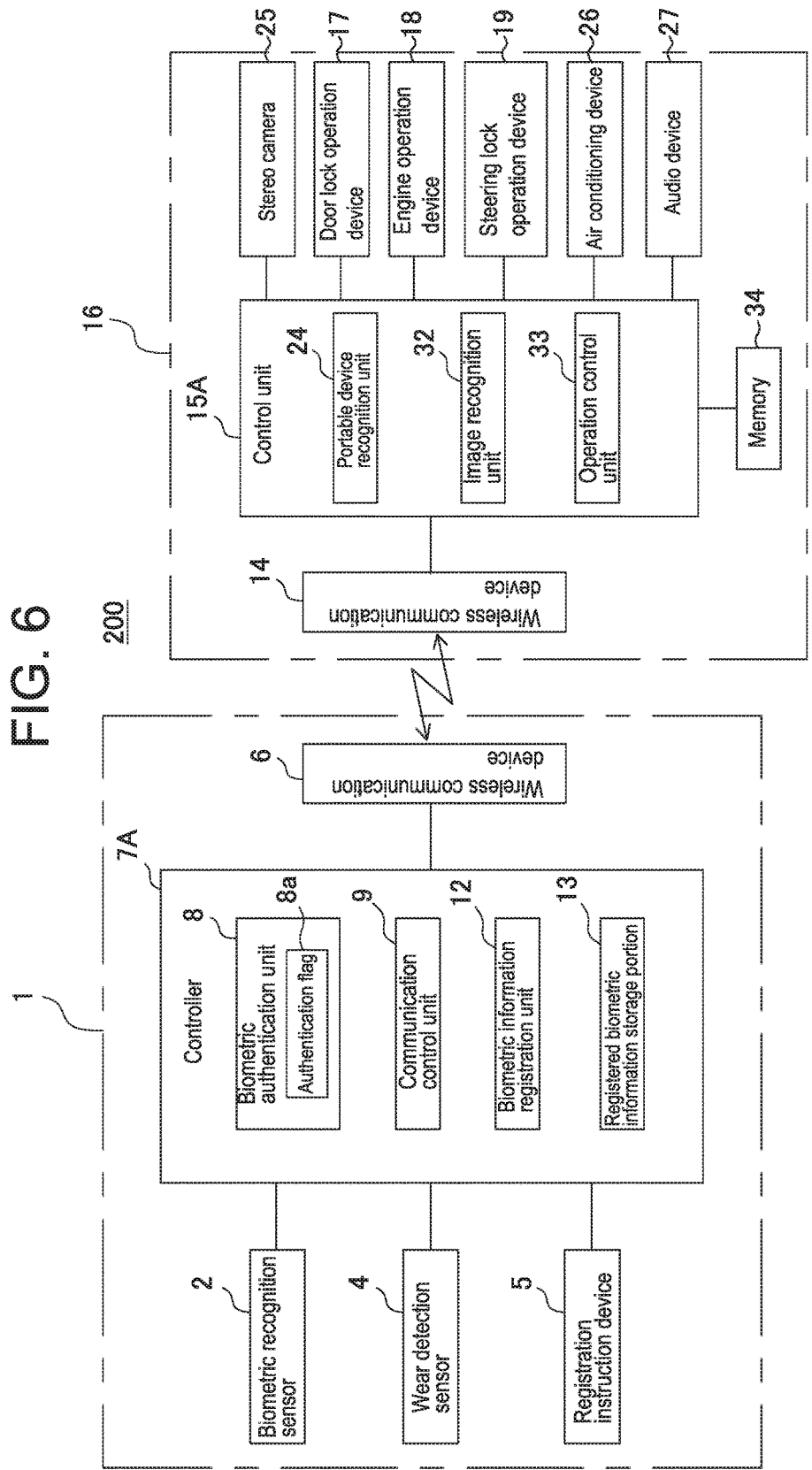
FIG. 6 is a block diagram of an entire configuration of an electronic key system of a second embodiment of the present invention.

FIG. 6 is a block diagram schematically illustrating an entire configuration of an electronic key system 200 of such an embodiment. In the following, description will be provided on operations of the electronic key system 200. Here, the same reference is given to an element commonly used in the electronic key system 100 and detailed description thereof will be skipped.

In the electronic key system 200, an imaging device is arranged at a position where imaging can be performed of a hand action of a user in the vicinity of a steering wheel of the automobile 16, for example, at a ceiling of a vehicle cabin. Owing to that a stereo camera 25 is used for the imaging device to image a hand action, it is possible to accurately detect the hand action while a shape, a distance, and a position of a hand to be imaged are recognized in three dimensions.

A control unit 15A is a main controller of the automobile 16 being configured of a CPU. The control unit 15A performs control processes of electronic devices mounted on the automobile 16 based on execution of previously-set software. FIG. 6 illustrates only the portable device recognition unit 24, an image recognition unit 32, and an operation control unit 33 that directly relate to operations of the electronic key system 200. These functions are actualized by executing the software.

Similarly to the abovementioned for the electronic key system 100, the portable device recognition unit 24 therein intermittently transmits a request signal requesting the portable device 1 to transmit an ID through the wireless communication device 14. When the portable device 1 entering a transmittal range of the request signal receives the request signal through the wireless communication device 6 and transmits the ID in correspondence thereto, the portable device recognition unit 24 compares the ID with the previously-set ID. When those are matched, wireless communication connection is established.

The image recognition unit 32 causes the stereo camera 25 to operate while the portable device recognition unit 24 recognizes the portable device 1. Then, a hand action of the user is detected by performing an image recognition process on three-dimensional image information of the hand action captured and output by the stereo camera 25. The process adopts a known method for recognizing a hand action by performing image processing on the three-dimensional image information of the hand action captured and output by the stereo camera 25, performing a binarization process using a previously-set standard pattern, and then, performing pattern matching of the binarized image using the standard pattern.

The operation control unit 33 controls operations of the door lock operation device 17, an engine operation device 18, the steering lock operation device 19, an air conditioning device 26, an audio device 27, and the like, in accordance with the hand action of the user recognized by the image recognition unit 32.

Figure 7:
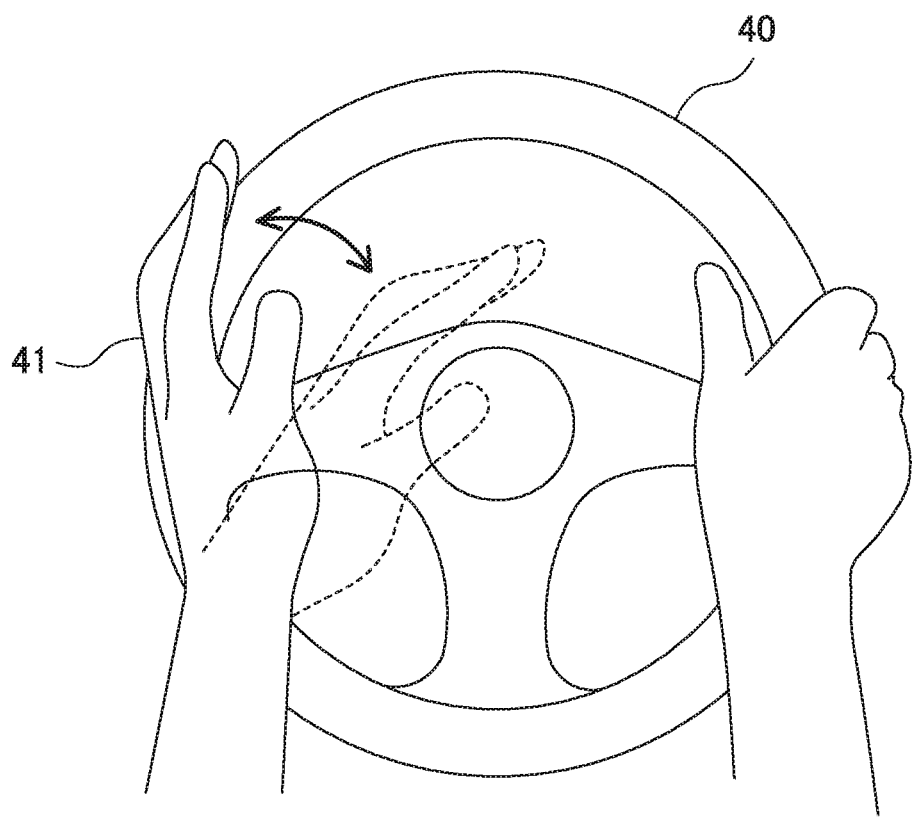
FIG. 7 is a schematic view illustrating a hand action to provide an instruction to an automobile in the electronic key system in FIG. 6.

For example, when the image recognition unit 32 detects an action of lateral swinging of a left hand palm 41 at a position near the steering wheel 40 as illustrated in FIG. 7, the operation control unit 33 outputs a drive signal to the engine operation device 18. Thus, regarding hand palm actions that are not performed normally during operating a steering wheel, such actions and operational instructions to the corresponding devices of the automobile 16 are set in a memory 34 in advance. In addition to lateral swinging of a hand palm, examples of such actions include an action of fingers varying from stone to scissors or paper and an action of thumbs-up.

Operations of the electronic key system 200 will be described with reference to flowcharts of FIGS. 8, 9A and 9B.

FIG. 8 is a flowchart indicating operations of the portable device 1. When the bracelet 20 is wound to and worn on an arm of a user and the buckle 22 is engaged, a wearing signal is input to the controller 7A from the wear detection sensor 4 (step S21) and the portable device 1 starts to operate.

Then, the controller 7A determines with the biometric authentication unit 8 whether biometric information is detected by the biometric recognition sensor 2 (step S22). Here, when the wearer 23 puts a finger on a package surface of the portable device 1, the biometric recognition sensor 2 outputs biometric information of a fingerprint. However, when a wear released signal is input from the wear detection sensor 4 before the biometric recognition sensor 2 outputs the biometric information ("YES" in step S23), the controller 7A determines that the portable device 1 is removed from the arm without placing a finger on the package surface of the portable device 1 after the portable device 1 is worn on the user and ends the operation.

When the wearer 23 places a finger on the package surface, the biometric authentication unit 8 compares the biometric information detected by the biometric recognition sensor 2 with registered biometric information stored in the registered biometric information storage portion 13 and determines whether or not the wearer 23 is a previously-registered user (step S24). In the case that the wearer 23 is not a registered user with an unmatched comparison result, a process of step S27 is performed. Operations thereof will be described later.

When the wearer 23 is authenticated as being a registered user with biometric information matching ("YES" in step S24), the biometric authentication unit 8 sets an authentication flag 8*a* indicating that the wearer 23 is the registered user (step S25). Then, when the authentication flag 8*a* has been set, the controller 7A causes wireless communication connection with the control unit 15A of the automobile 16 to be available (step S26). Here, the wireless communication connection available state represents a state in which the portable device 1 can transmit an ID through the communication control unit 9 in response to a request signal that is transmitted by the control unit 15A of the automobile 16 through the portable device recognition unit 24.

Then, the controller 7A determines whether or not a wear released signal is input from the wear detection sensor 4 (step S27). When a wear released signal is not input, setting of the authentication flag 8*a* is checked (step S28). Then, when the authentication flag 8*a* has been set, it returns to the process of step S26. Thus, while a wear released signal is not input from the wear detection sensor 4 and the authentication flag 8*a* is in a set state, the controller 7A can perform wireless communication with the control unit 15A as in step S26.

Here, when the portable device 1 is removed from the arm of the wearer 23 and a wear released signal is input from the wear detection sensor 4 ("YES" in step S27), the controller 7A ends the operation after resetting the authentication flag 8*a* (step S29). Thus, wireless communication becomes unavailable by resetting the authentication flag 8*a*.

In the following, description will be provided on operations of the controller 7A when it is determined that the wearer is not a registered user with an unmatched comparison result of the biometric information in step S24. In this case, the authentication flag 8*a* is not set and a process of step 27 is performed with wireless communication with the control unit 15*a* being unavailable. Then, a wear released signal is not input from the wear detection sensor 4 and a process of step 28 is performed. Here, since the authentication flag 8*a* has not been set ("YES" in step S28), the controller ends the operation. Thus, even when an authorized user wears the portable device 1, the controller 7A does not perform wireless communication with the control unit 15A.

In the following, operations of the control unit 15A of the automobile 16 with respect to the abovementioned operations on the portable device 1 side will be described with reference to FIGS. 9A and 9B. FIG. 9A is a flowchart illustrating operations of the control unit 15A for portable device recognition. The control unit 15A transmits, with the portable device recognition unit 24, a request signal requesting the portable device 1 to transmit an ID (step S41).

Accordingly, when the portable device 1 authenticated by the biometric authentication unit 8 that the wearer is a registered user enters a transmittal range of the request signal, the controller 7A transmits a previously-set ID through the wireless communication device 6 by performing the process in step S26 (FIG. 8). When the ID is transmitted, the portable device recognition unit 24 determines whether the ID is matched with the previously-set ID (step S42). When those are matched, existence of the portable device 1 is recognized (step S43). Thus, authentication between the controller 7A and the control unit 15A is established.

The control unit 15A outputs a door lock release signal to the door lock operation device 17 to release door lock (step S44), operates the stereo camera 25 (step S45), and then, ends the routine of the portable device recognition process.

After recognizing existence of the portable device 1, the control unit 15A executes previously-determined control processes of electronic devices mounted on the automobile 16, while performing, as timer interrupt, a process of image recognition illustrated in a flowchart of FIG. 9B.

In this interrupt process, first, the control unit 15A determines whether communication connection with the portable device 1 is available through the portable device recognition unit 24 (step S51). In this case, the determination is performed based on whether or not an ID is transmitted from the portable device 1 in response to a request signal transmitted from the portable device recognition unit 24. As described above, wireless communication connection with the portable device 1 is available while the authentication flag 8*a* has been set.

When communication with the portable device 1 is available, the control unit 15A detects, with the image recognition unit 32, a hand action of a user from an image captured and output by the stereo camera 25 (step S52). Then, the operation control unit 33 determines whether the detected hand action corresponds to an action to instruct an operation to a device of the automobile 16 (step S53). When the hand action corresponds to an action instructing an operation, the operation control unit 33 outputs an operation signal to a corresponding device and returns to a process before the interrupt (step S54). Thus, for example, an on/off signal or a temperature adjust signal is output to the air conditioning device 26 and a volume adjust signal or the like is output to the audio device 27, as instructed by the user.

In contrast, when it is determined that communication connection with the portable device 1 is not available in step S51, the control unit 15A stops operation of the stereo camera 25 (step S55). Then, the control unit 15A returns to a process before the interrupt, and thereafter, does not perform the interrupt process of image recognition. Thus, after the portable device 1 is recognized and door lock is released, the control unit 15A does not provide any instruction to the automobile 16 even when another person without the portable device 1 worn gets on the vehicle and moves a hand.

As describe above, according to the electronic key systems 100, 200 of the present invention, biometric information is input after a wearing signal is generated when a user wears the portable device 1. Then, when the input biometric information is matched with previously-registered biometric information, the wearer is authenticated as an authorized user registered in advance. After the authentication, according to the electronic key system 100, the user can provide instructions to the automobile 16 with actions of an arm wearing the portable device 1. According to the electronic key system 200, after existence of the portable device 1 is recognized, door lock of the automobile 16 is released, and then, a user being in a cabin can provide instructions with predetermined action of a hand palm.

Here, in the electronic key systems 100, 200 described above, the biometric authentication unit 8 and the registered biometric information storage portion 13 are arranged in the controller 7, 7A of the portable device 1. However, those may be arranged at the cloud to be connected through a communication line such as the internet.

Figure 10:
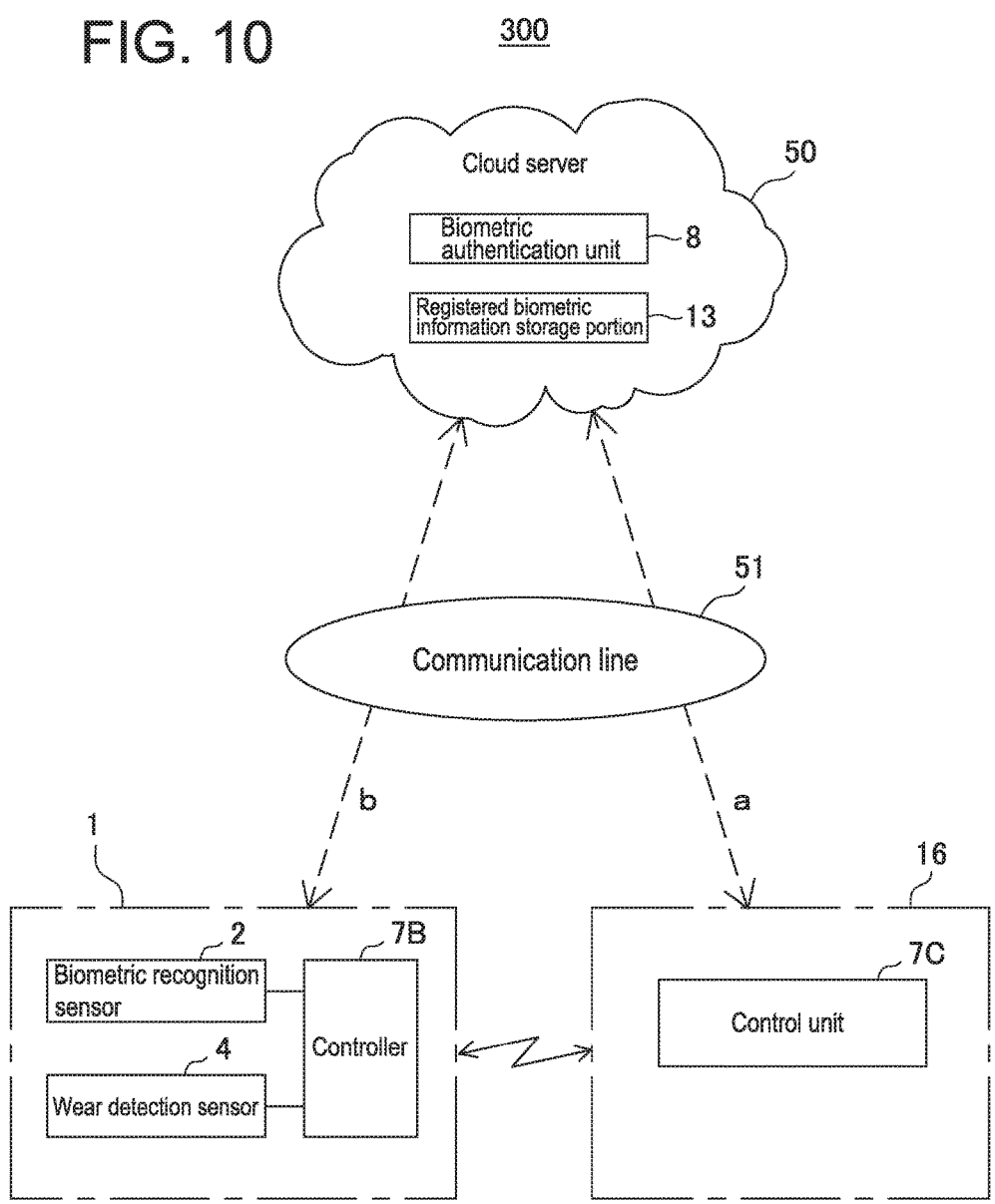
FIG. 10 is a schematic view of an electronic key system of a third embodiment of the present invention.

FIG. 10 is a schematic diagram of an electronic key system 300 in which the biometric authentication unit 8 and the registered biometric information storage portion 13 are arranged in a cloud server 50.

In FIG. 10, after the controller 7B of the portable device 1 detects with the wear detection sensor 4 that the portable device 1 has been worn by a user and detects with the biometric recognition sensor 2 biometric information of the wearer, the biometric authentication unit 8 of the cloud server 50 determines matching with biometric information of the registered user.

In this case, for transmitting the biometric information of the wearer detected by the biometric recognition sensor 2 through a communication line 51, there are method a and method b. With method a, the biometric information is transmitted first to the control unit 7C of the automobile 16 from the controller 7B of the portable device 1, and then, transmitted to the cloud server 50 from the control unit 7C. With method b, the portable device 1 directly accesses the cloud server 50 and transmits the biometric information to the cloud server 50. In the case with method b, it is preferable that the portable device 1 is a wireless terminal portable device such as a smart phone and a tablet-type computer capable of being connected to the cloud server 50 through the communication line 51.

Here, similarly to the electronic key systems 100, 200, in the electronic key system 300 as well, the biometric recognition sensor 2 and wear detection sensor 4 are arranged in the portable device 1. Further, the control unit 7C of the automobile 16 intermittently transmits, through the wireless communication device 14, a request signal requesting the portable device 1 to transmit an ID. The portable device 1 has a function, being similar to the electronic key systems 100, 200, to transmit the ID in response to the request signal.

Figure 11:
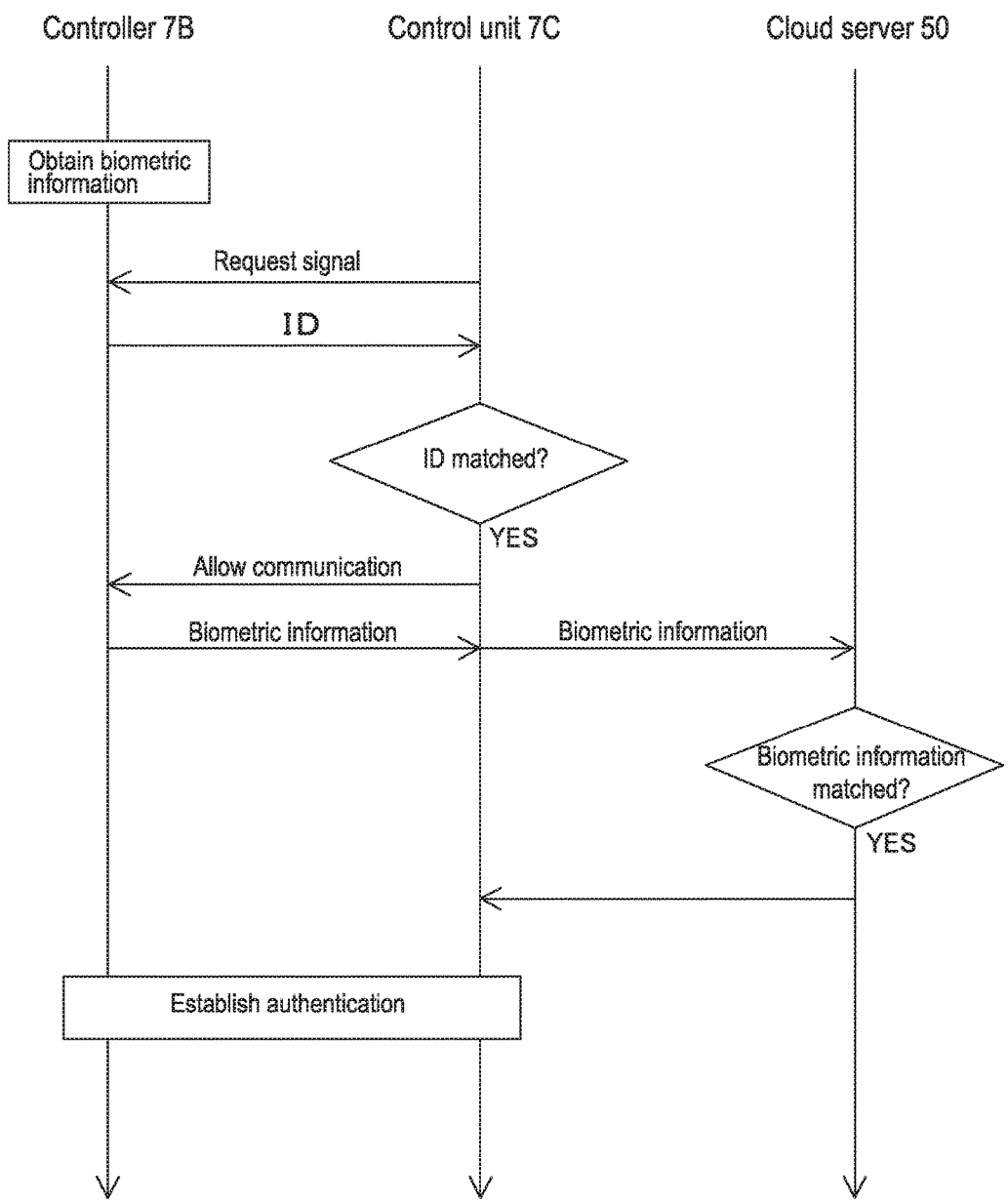
FIG. 11 is a sequence diagram until authentication is established between a portable device and an automobile of the electronic key system in FIG. 10.

FIG. 11 is a sequence diagram illustrating processes until authentication between the controller 7B of the portable device 1 and the control unit 7C is established with the method a to transmit the biometric information transmitted from the portable device 1. When wearing of the portable device 1 is detected by the wear detection sensor 4 and biometric information is obtained by the biometric recognition sensor 2, the controller 7B transmits an ID in response to receiving a request signal transmitted from the control unit 7C.

When the transmitted ID is matched with a previously-stored ID, the control unit 7C allows communication and the controller 7B transmits the obtained biometric information to the control unit 7C. The control unit 7C transmits the biometric information to the cloud server 50 and the cloud server 50 determines whether the biometric information is matched with biometric information stored in the registered biometric information storage portion 13. Thus, authentication between the control unit 7C and the controller 7B is established.

Figure 12:
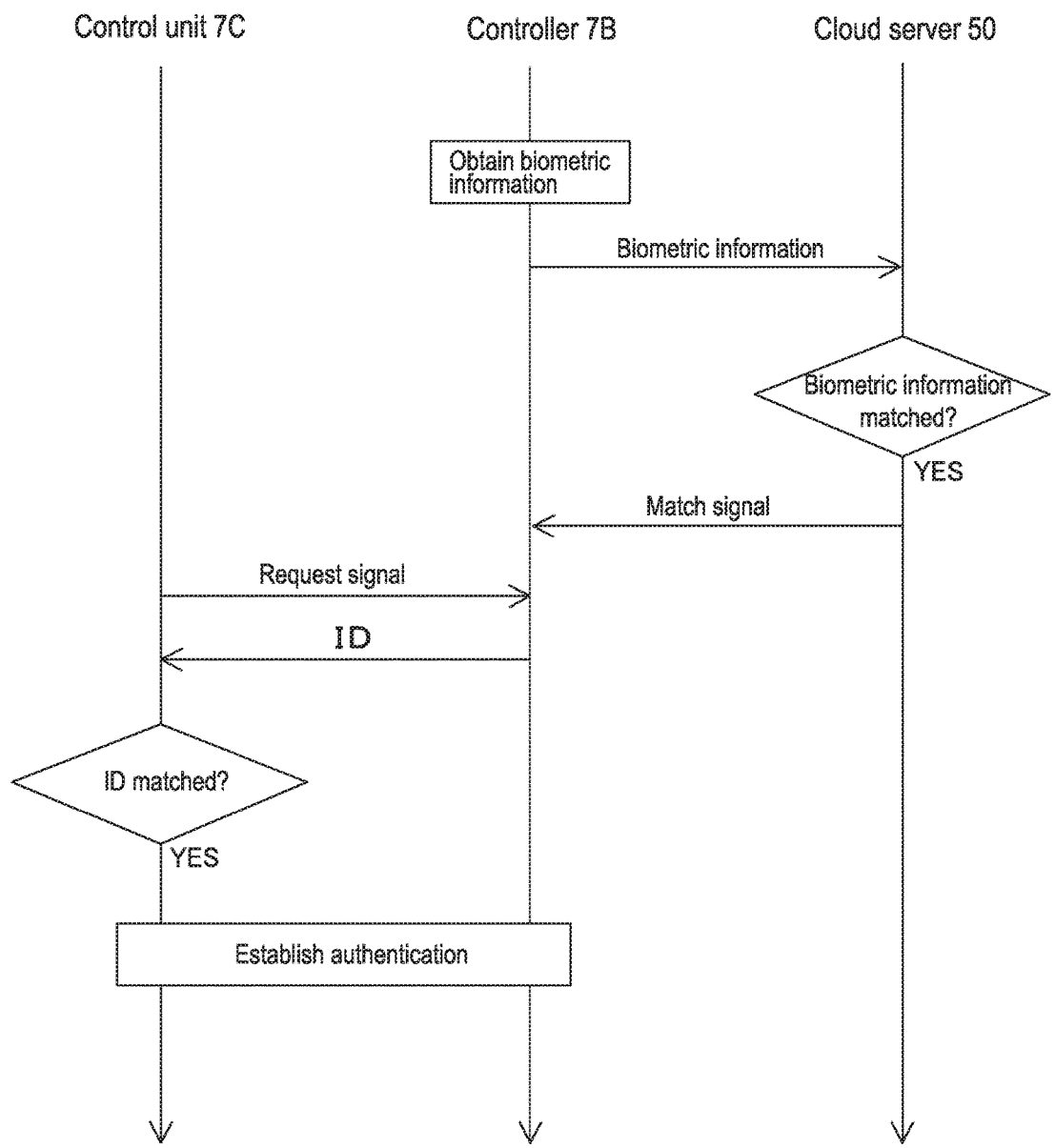
FIG. 12 is a sequence diagram of another example until authentication is established between the portable device and the automobile of the electronic key system in FIG. 10.

FIG. 12 is a sequence diagram illustrating processes until authentication between the controller 7B of the portable device 1 and the control unit 7C is established with the method b to directly transmit biometric information obtained by the portable device 1 to the cloud server 50. In this case, when wearing of the portable device 1 is detected by the wear detection sensor 4 and biometric information is obtained by the biometric recognition sensor 2, the controller 7B transmits the biometric information to the cloud server 50.

The cloud server 50 determines whether the biometric information is matched with biometric information stored in the registered biometric information storage portion 13. If those are matched, the cloud server 50 transmits a match signal to the controller 7B. After receiving the match signal, the controller 7B transmits an ID in response to receiving a request signal transmitted from the control unit 7C.

When the transmitted ID is matched with a previously-stored ID, the control unit 7C allows communication to establish authentication between the control unit 7C and the controller 7B.

Then, when authentication between the controller 7B and the control unit 7C is established with sequence flow illustrated in FIG. 11 or FIG. 12, as described for the electronic key system 100, according to an action of a region of a user wearing the portable device 1 (not illustrated), an operation code to the automobile is transmitted to the control unit 7C. Alternatively, as described for the electronic key system 200, the control unit 7C detects a hand action of a user wearing the portable device 1 and controls operation of the automobile in accordance therewith.

Owing to that biometric information of registered users is stored in the cloud server 50 and biometric authentication is performed in the cloud server 50, authentication can be established between the single portable device 1 and a plurality of control units of automobiles. Accordingly, for an owner of a plurality of automobiles, a car rental agency, and the like, it is possible to remove inconvenience to manage a portable device 1 for each automobile.

Further, in addition to biometric information, it is possible to store preference information (i.e., calibration) regarding driving individualistic for each user, for example, information regarding a seat position, addresses of a home and an office, frequently-visiting places and stores, a driving style, a sleepy time range, inter-vehicle distance to a preceding vehicle corresponding to speed, brake timing corresponding to inter-vehicle distance, and the like. In such a case, especially for an automobile with automatic driving, it is possible to automatically provide a travelling state preferable for each user and transference to a destination by downloading the information.

In the following, description will be provided on automated driving. It relates to automated driving systems that have been researched and developed recently for further improving safety of road traffic. With such an automated driving system, an automobile automatically travels while recognizing circumstances thereround. In Japan, automation degree of automated driving systems for vehicles such as automobiles is defined as being classified into four levels, from Level 1 to Level 4. Level 1 is called a safe driving assisting system with which any of accelerating, steering, and braking is performed by an automobile. Level 2 is called a quasi-automated-driving system with which a plurality of operations among accelerating, steering, and braking is performed by an automobile. Level 3 is also called a quasi-automated-driving system with which all of accelerating, steering, and braking are performed by an automobile while those are performed by a driver only in a case of emergency. Level 4 is called a completely automated driving system with which all of accelerating, steering, and braking are performed something other than a driver completely without involvement of the driver. Here, an automated driving system represents Level 2 through Level 4 ("strategic innovation program (SIP) automated driving system research and development plan", Nov. 13, 2014, Cabinet Office, Director-General for Policy Planning, Science Technology and Innovation Department). Here, the automated driving is defined to include automated driving at all automation degrees, Level 1 to Level 4.

With such an automated driving vehicle, it is possible to actualize automated driving that fits for each user by obtaining calibrations of the user with biometric authentication.

In the above, description is provided in detail on preferable embodiments of the present invention. Here, not limited thereto, the present invention may be actualized with a variety of modifications within the technical scope thereof. For example, not limited to a bracelet that is to be worn on a user, the portable device 1 may be a finger ring, a head band, a necklace, a pendant, or the like. Further, not limited to an arm or a hand palm, a user action may be an action of a head.

EXPLANATION OF REFERENCES 100, 200, 300 Electronic key system
1 Portable device
2 Biometric recognition sensor
4 Wear detection sensor (Wear detection unit)
6 Wireless communication device
8 Biometric authentication unit
9 Communication control unit
10 Action detection unit
13 Registered biometric information storage portion (Registered biometric information storage unit
14 Wireless communication device
15 Control unit
16 Automobile
25 Stereo camera (Imaging device)
32 Image recognition unit
33 Operation control unit

The invention claimed is:

1. An electronic key system comprising:
a control unit mounted on an automobile to provide an operational instruction to the automobile,
a portable device configured to be worn on and carried by a body region of a user and including at least a biometric recognition sensor configured to detect biometric information of the user,
a registered biometric information storage unit configured to store biometric information of a previously-registered user; and
a biometric authentication unit configured to determine whether or not biometric information of the user detected by the biometric recognition sensor is matched with the previously-registered biometric information of the user stored in the registered biometric information storage unit,
wherein
the control unit includes an imaging device, an image recognition unit and an operation control unit,
authentication between the portable device and the control unit is established when the user is authorized as the registered user by the biometric authentication unit, and
while the authentication is established, the imaging device images an action of a region of the user inside the automobile, the image recognition unit detects a specific action of the region of the user based on the image information from the imaging device, and the operation control unit controls an operation of the automobile in accordance with the specific action of the region of the user detected by the image recognition unit.

2. The electronic key system according to claim 1, wherein the portable device further includes a wear detection unit, and
the biometric authentication unit performs determination of matching with the biometric information when the wear detection unit detects wearing onto the user and establishes authentication between the portable device and the control unit when the biometric information is matched.

3. The electronic key system according to claim 2, wherein the biometric authentication unit releases the authentication when the wear detection unit detects that the user has removed the portable device after establishment of the authentication.

4. The electronic key system according to claim 1, wherein the control unit includes a portable device recognition unit configured to recognize the portable device with which the user is authorized as the registered user by the biometric authentication unit.

5. The electronic key system according to claim 1, wherein the registered biometric information storage unit and the biometric authentication unit are arranged at a cloud server.

6. The electronic key system according to claim 5, wherein the control unit transmits the biometric information transmitted from the portable device to the cloud server and establishes authentication with the portable device based on a determination result of the biometric authentication unit.

7. The electronic key system according to claim 5, wherein the portable device transmits the biometric information to the cloud server and establishes authentication with the control unit based on a determination result of the biometric authentication unit.

8. The electronic key system according to claim 5, wherein the registered biometric information storage unit further stores preference information regarding automobile driving of the user corresponding to the stored biometric information in the registered biometric information storage unit, and
the control unit downloads the preference information when authentication with the portable device is established.

9. The electronic key system according to claim 1, wherein the action detection unit comprises an acceleration sensor and an angular velocity sensor.

10. The electronic key system according to claim 1, wherein the registered biometric information storage unit and the biometric authentication unit are arranged at the portable device.

11. The electronic key system according to claim 10, wherein the portable device includes an action detection unit configured to detect a movement of the portable device worn on the body region of the user, and an operation instruction unit configured to generate an operation code and transmit it to the control unit in accordance with the movement of the portable device detected by the action detection unit and associated to a specific action of the body region of the user.

12. The electronic key system according to claim 9, wherein the action detection unit determines from a movement amount and a movement angle of the portable device detected by the acceleration sensor and the angular velocity sensor whether a type of a reciprocating action performed by the portable device is a swing action or a linear action, and based on the type of the reciprocating action determines a type of the specific action of the body region of the user.

13. The electronic key system according to claim 1, wherein when the authentication between the portable device and the control unit is established, the control unit releases door lock of the automobile and starts operation of the imaging device.

14. The electronic key system according to claim 3, wherein when the authentication is released, the control unit stops operation of the imaging device.

* * * * *